United States Patent [19]

Hulls et al.

[11] Patent Number: 5,895,791
[45] Date of Patent: Apr. 20, 1999

[54] INSULATING FOAMS AND THE MANUFACTURING THEREOF

[75] Inventors: Byron J. Hulls, Newark; Vyacheslav Grinshpun, Granville, both of Ohio

[73] Assignee: Owens Corning Fiberglas Technology, Summit, Ill.

[21] Appl. No.: 08/999,422

[22] Filed: Dec. 12, 1997

Related U.S. Application Data

[62] Division of application No. 08/410,607, Mar. 24, 1995.

[51] Int. Cl.⁶ .................................................. C08J 9/14
[52] U.S. Cl. ........................ 521/132; 521/97; 521/98; 521/130
[58] Field of Search ....................... 521/98, 132, 97, 521/130, 181

[56] References Cited

U.S. PATENT DOCUMENTS

| | | |
|---|---|---|
| 3,577,363 | 5/1971 | Klug. |
| 3,607,796 | 9/1971 | Eberle. |
| 3,912,665 | 10/1975 | Spitzer et al.. |
| 3,912,666 | 10/1975 | Spitzer et al.. |
| 3,912,667 | 10/1975 | Spitzer et al.. |
| 3,975,316 | 8/1976 | Villa ................................ 521/132 |
| 4,167,612 | 9/1979 | Tucker et al. ..................... 521/132 |
| 4,271,272 | 6/1981 | Strickman et al. ................ 521/132 |
| 4,303,729 | 12/1981 | Torobin. |
| 4,328,319 | 5/1982 | Osipow et al.. |
| 4,394,457 | 7/1983 | Ogasa. |
| 5,035,833 | 7/1991 | Ogawa et al.. |
| 5,205,956 | 4/1993 | Volkert et al.. |
| 5,272,182 | 12/1993 | Burnell. |
| 5,405,885 | 4/1995 | Sampara et al. .................. 521/132 |
| 5,451,615 | 9/1995 | Birch ................................ 521/132 |
| 5,532,284 | 7/1996 | Bartlett et al.. |

FOREIGN PATENT DOCUMENTS

| | | |
|---|---|---|
| 676381 | 7/1952 | United Kingdom. |
| 9114724 | 10/1991 | WIPO. |

*Primary Examiner*—Morton Foelak
*Attorney, Agent, or Firm*—C. Michael Gegenheimer

[57] ABSTRACT

This invention relates to insulating foams and to a process for producing the foams. Preferably, the foams are made from phenol formaldehyde resins. The blowing agents for making the foams include film forming coating material which coats the interior surfaces of the foam cells. The coated foams have better thermal conductivity.

12 Claims, No Drawings

INSULATING FOAMS AND THE MANUFACTURING THEREOF

CROSS REFERENCE TO RELATED APPLICATION(S)

This is a division of U.S. patent application Ser. No. 08/410,607, filed Mar. 24, 1995.

TECHNICAL FIELD

This invention relates to synthetic insulating foams based on polymeric materials. These foams could be derived from the thermoplastic resins such as polystyrene or polyethylene, or from more basic organic molecules such as phenol and formaldehyde, or isocyanate and polyol forming a thermoset type of polymeric foam. The invention also primarily relates to the manufacture of these closed cell foams.

BACKGROUND ART

Insulating synthetic foams have found various application in contemporary society. One of the most voluminous applications of these foams is in the construction field, as insulators for walls, roofs, basements, etc. More specialized applications for these foams include appliances (refrigeration), pipes, ducting, auto, aerospace and marine industries.

Despite expanding applications and ever increasing production of insulating foams, their thermal insulating properties especially their long term insulating properties did not improve in the last decade, but have somewhat suffered due to the switch to environmentally friendly blowing agents. Improvements in the insulating properties of these foams, especially their low density variety will save a lot of energy, reduce the consumption of fossil fuels and improve the environment due to the reduction in greenhouse gases formed by the combustion of fossil fuels.

DISCLOSURE OF INVENTION

We now have discovered a process for producing insulating foam which provides a foam with improved thermal conductivity. The process uses a blowing agent containing film forming coating material. The coating material admixes or dissolves in the blowing agent. During the foaming step, closed cells form, each cell having interior surfaces. During foaming, the coating material also continuously coats the interior surfaces of each cell. By virtue of this film forming coating, a barrier to air ingress and insulating gas egress forms. The coating and cell walls behave as multilayered barrier films.

Liquid or solid coating materials, inorganic, organic, oligomeric or polymeric, synthetic or naturally derived are mixed with or dissolved in a blowing agent which is subsequently used to blow a cellular structure. The cellular structure is produced of an inorganic, organic or polymeric material which is not soluble or has a very limited solubility in the coating material. During the blowing process when cell structures, such as windows and struts, are formed, the coating material precipitates out of gaseous phase of the blowing agent and forms layers on the cell structure surface. Blowing agents used in this invention could be various CFCs, HCFCs, HFCs, inorganic gases like $CO_2$, $N_2$, alkanes or any other agent used to expand cellular materials. The layered structure formed in this process has a lower gas permeability than known foam materials and as such prevents the ingress of air and loss of blowing agent and reduces the loss of thermal insulating value. Our process improves thermal (especially aged thermal) properties of the cellular materials. The process also may improve mechanical properties of the cellular materials at a given density. The invention improves processing of non-CFC blown foams, where non-CFC blowing agent has high solvency and/or low boiling point.

BEST MODE OF CARRYING OUT THE INVENTION

Our process includes the steps of:

(a) providing a foaming composition of;

(b) a blowing agent;

(c) a surfactant; and (d) a catalyst;

mixing the composition to initiate foaming and to produce a resol foam; and curing the foam to a density ranging from 0.5 to 3.0 pounds per cubic foot.

This process allows us to foam phenol formaldehyde resins which have a very high viscosity and cure the foams to a very low density.

The foam is made from foaming compositions of thermo setting and thermoplastic materials such as polyethylene, polypropylene, polyesters, polyurethanes, dichloro-trifluoro ethylene, polyvinyl fluoride polyvinylidene, polymethyl methacrylate acetyl, phenol-formaldehyde resins and silicone and polycarbonate resins. Preferably, the foaming composition is made from phenol formaldehyde resin. More preferably, the composition is a phenol formaldehyde resol resin having substantially no free formaldehyde and having a water content of 4 to 8% and a viscosity ranging from 5,000 cps to 40,000 cps at 40° C.

The interior surface defining each of the cells of the foam is continuously covered with a film of a polymer. Illustrative of the polymers suitably used in this invention are to coat the cells of the foam are polyvinyl alcohol, polyacrylic acid, polyvinyl pyrrolidone and polyethylene glycol. We have found polymethacrylate to be especially useful. Good results are also obtained with mineral and vegetable oils.

The blowing agent can be selected from a number of HCFCs or hydrofluorocarbons (HFCs). Specific examples of these blowing agents include 1-chloro- 1,1-difluoroethane (142b), dichlorofluoro-methane (22), 2-chloro- 1,1,1,2-tetrafluoroethane (124), 1,1-difluoroethane( 152a), pentafluoroethane(125) and 1,1,1,2-tetrafluoroethane, dichlorflouro ethane (141b) or others.

The blowing agent also may include a perfluoroalkane wherein the perfluoroalkane comprises 1 to 5 weight percent of the total blowing agent weight. Preferably, the perfluoroalkane is represented by the formula:

wherein n is an integer ranging from 4 to 20, x is zero or an integer ranging from 2 to 10, and x+y=2n+2. Specific examples of the perfluoroalkane include dodecafluoropentane, tetradecafluorohexane, hexadecafluoroheptane.

Preferably the perfluoroalkane comprises 1 to 3 weight percent and more preferably, 1 to 2 weight percent of total blowing agent weight. Alkanes like butane, pentane or cyclopentane also could be employed.

Surfactants which are generally used for phenolic foam manufacture are typically non-ionic in nature. Surfactants containing silicon are widely used, such as the silicon ethylene oxide/propylene oxide copolymers of alkoxy silanes, polysilyl/phosphonates, polydimethylsiloxane and polyoxyalkylene copolymers. Examples of suitable commercial silicon-containing surfactants are the Dow Corning Trademarks DC-190 and DC-193 and the Union Carbide Trademarks L-530, L-5310 and L-5410. Other non-ionic surfactants are suitable including the Pluronic (trademark of BASF Wyandotte) non-ionic surfactants, particularly the high molecular weight F-127, F-108 and F-98 polyethylene-polypropylene oxides.

Surfactant concentrations can vary from 2 to 10% of the total formulation weight. The preferred level for the resoles described herein is 2 to 5%. To produce closed cell foams which contain the blowing agent in sufficient amounts to give superior thermal values, careful selection of resin and surfactant properties is required.

The catalysts employed are usually acids. Under certain circumstances, foam may be generated solely by the application of heat without the use of a catalyst. In practice, however, a catalyst is necessary to complete the curing of the foams.

Numerous acid catalysts, both organic and inorganic, are known and disclosed in the prior art. Examples of inorganic acids include hydrochloric acids, sulfuric acids, nitric acid and the various phosphoric acids. Examples of organic acids include aromatic sulfuric acids, such as benzene sulfonic acid, toluene sulfonic acid, xylene sulfonic acid, phenol sulfonic acid and naphthalene sulphonic acid; latent acid catalysts such as phenol esters of carboxylic acids including phenyl trifluoroacetate and phenyl hydrogen maleate and various sulfur dioxide containing compounds such as the sulfur of a,-unsaturated ketones and aldehydes and various dienes; mono and poly carboxylic acids such as acetic acid, formic acid, propionic acid, oxalic acid, maleic acid and strong substituted organic acids such as trichloracetic acid. An admixture of toluene sulphonic acid is usually preferred. The acid catalyst sold under the trademark Ultra TX (Witco Chemical Company), the xylene-toluene sulfonic acids are especially preferred.

The cured resol foam has a density ranging from 0.5 to 3.0 pounds per cubic foot. Preferably the resol foam density ranges from 0.7 to 1.8 pounds per cubic foot. The resol resin preferably has a viscosity ranging from 5,000 cps to 40,000 cps at 40 °C. Preferably the resol resin has a viscosity ranging from 8,000 cps to 20,000 cps at 40° C.

The basic steps for preparing foams from resol resin are as follows:

(a) preparation of the resol resin;
(b) addition of any modifying agent;
(c) neutralizing the resin;
(d) stripping off water, e.g. by vacuum stripper;
(e) adding the surfactant;
(f) adding a blowing agent and coating material;
(g) adding an acid catalyst and allowing the mixture to foam; and
(h) curing the foam.

The foams are prepared from resols which have been made using conventional starting mole ratios of phenol to formaldehyde, in the present case in the range of 1:1 to 1:4.5, preferably 1:1.5 to 1:2.5. The high mole ratio materials are the basis for resins which are substantially free of phenol and which can be treated with a formaldehyde co-reactant or scavenger, to reduce the initially high free formaldehyde content.

The resin is concentrated to reduce the free water content of the resin. A typical viscosity resin used for manufacturing resol foam has a viscosity in the order of 5,000 to 40,000 cps and a free water content of 4 to 8%. However, during the manufacture of phenolic foams from high viscosity resins in accordance with the present invention, the resin utilized will preferably have a viscosity in the order of 8,000 to 20,000 cps at 40° C.

We also may use a ramping postcure procedure according to the following:

0 to 70 minutes at 75–85° C. followed by
20 to 105 minutes at 90–95° C. followed by
60 to 170 minutes at 100–105° C.

EXAMPLE 1

Preparation of Resol

The resol resin used in the production of these foams used a formaldehyde:phenol (F/P) mole ratio of 2.3:1, using 52% formaldehyde and 99% phenol. The reaction was carried out under basic conditions at elevated temperatures with 50% caustic solution. When the Ostwald viscosity of the resin reached 62cst (measured at 25°), the reaction was cooled and neutralized with 50% aqueous aromatic sulphonic acid. Urea was added as a formaldehyde scavenger at a level of 77% by mole of the residual formaldehyde. The resin was passed through a thin film evaporator to reduce the water content from about 30% to 4–8%. An ethylene oxide based nonionic surfactant Pluronic F127 from BASF was then added in the molten state at 3.5% by weight of the resin and mixed into the resin to form a homogeneous mixture. The final viscosity of the resin was 9000–12000 cps (measured at 40° C.).

EXAMPLE 2

Preparation of Resol Foam

The resol foam was prepared by mixing together the resol resin and surfactant with the blowing agent and acid catalyst using a high shear short residence, rotor/stator continuous mixer. The blowing agent was saturated with nitrogen at 200 psi prior to introduction in the high shear mixer. The foaming catalyst was a blend of resorcinol, diethylene glycol, and a mixture of xylene and toluene sulphonic acids. (See U.S. Pat. Nos. 4,883,824 and 4,945,077). The resol resin, blowing agent, and catalyst were continuously metered to the mixer by means of suitable flow metering devices in the following ratios:

| | |
|---|---|
| resin/surfactant | 100 |
| HCFC141b | 8.63 |
| catalyst* | 11.8 |

*mixture of xylene and toluene sulphonic acids.

The foamable mixture (resin/surfactant, blowing agent, catalyst) exited the mixer through evenly spaced tubes and nozzles to form continuous beads of froth on a moving facer. This resulted in parallel lines of foam which knitted together, as the froth expanded, to form a continuous sheet. The foam sheet then moved through a conveyor oven at approximately 80° C. at a fixed rate to produce a board that was cured enough to handle. The boards underwent further curing using the following postcure cycle:

25 minutes at 75° C. followed by
25 minutes at 85° C. followed by
50 minutes at 90° C. followed by
25 minutes at 95° C. followed by
25 minutes at 100° C. followed by
50 minutes at 105° C.

EXAMPLE 3
No Blowing Agent Additive—Standard Foam

We prepared foam containing 52.25 parts phenolic resin (formaldehyde:phenol ratio 2.3:1, free water 6.5%, viscosity 12,000 cps). It was preblended with 2.75 parts of an equal blend of Harfoam PI (Huntsman Chemical Company) and Pluronic F127 (BASF).

Into this was blended in a cup, 17 parts of HCFC141B (Atochem). To this was added rapidly and with vigorous stirring 5 parts of a catalyst composed of a blend of resorcinol, diethylene glycol and a mixture of xylene and toluene The resultant foam was removed from the mold hot and stored five days at room temperature, at which point the thermal conductivity was found to be 0.262 Btu$\times$in h$^{-1}$ ft$^{-2}$ F$^{-1}$ with a density of 1.5 pcf (24 kg/m$^3$). The foam had a very course structure and an average cell size of 280μ.

EXAMPLE 4
1% PMMA in Blowing Agent 1 part polymethylmethacrylate (average MW 120,000 Aldrich) was dissolved in 99 parts HCFC 141b (Atochem) in a closed container at 28% C (a).

A foam was prepared as in Example 3, but using 11 parts of the prepared blowing agent and additive (a).

The resultant foam had a fine cell structure and a thermal conductivity of 0.144 Btu$\times$in h$^{-1}$ ft$^{-2}$ °F$^{-1}$ at density of 1.5 pcf or 24 kg/m$^3$. SEM photographs indicate layers of material on the cell walls and struts.

EXAMPLE 5
10% PMMA in Blowing Agent 10 parts polymethylmethacrylate (average MW 120,000—Aldrich) was dissolved in 90 parts HCFC 141b (Atochem) in a closed container at 28° C. (b).

A foam was prepared as in Example 3, but using 11 parts of the prepared blowing agent and additive mix (b).

The resultant foam had a fine cell structure and a thermal conductivity of 0.138 Btu$\times$in h$^{-1}$ ft$^{-2}$ °F$^{-1}$ at density of 1.5 pcf or 24 kg/m$^3$. SEM photographs indicate layers of material on the cell walls and struts. The average cell size was 150μ.

EXAMPLE 6
5% Oil and 1% Rexol 65/10

5 parts sunflower oil (edible grade) and 1 part surfuctant Rexol 65/10 (Huntsman Chemical Company) were dissolved in 94 parts Freon 113 (DuPont) (c).

We used 36.1 parts of the phenol formaldehyde resin in Example 1 were blended with 1.9 parts of the surfactant blend from Example 3 and 14 parts of the blowing agent blend (c) were blended and a foam was prepared using 4.5 parts of the catalyst blend described in Example 3.

The resultant foam had a fine cell structure with an oily sheen and a thermal conductivity of 0.129 Btu$\times$in h$^{-1}$ ft$^{-2}$ °F$^{-1}$ at density of 1.5 pcf or 24 kg/m$^3$. SEM photographs show droplets and wetted areas on the cell walls and struts.

We claim:

1. An insulating foam resulting from:

a foaming composition comprising:
   (i) a phenol-formaldehyde resin; and
   (ii) a blowing agent admixed with a film-forming additive, said film forming additive comprising a mineral or vegetable oil; and said insulating foam having coated cells with interior wall surfaces continuously coated with the film-forming additive; and said insulating foam having a density ranging from 0.5 to 3.0 pounds per cubic foot and a thermal conductivity of less than 0.200 BTU$\times$in h$^{-1}$ ft$^{-2}$ °F$^{-1}$.

2. A foam according to claim 1 where the phenol-formaldehyde resol resin has substantially no free formaldehyde, a water content of 4 to 8%, a viscosity ranging from 5,000 to 40,000 cps at 40° C., and the foam is a closed-cell resole foam.

3. A foam according to claim 1 wherein the cell walls and film forming coating form multilayered barrier films.

4. A foam according to claim 1 wherein the interior wall surfaces continuously coated with the film-forming additive provide a barrier to air ingress into and insulating gas egress from the cells.

5. A foam according to claim 1 wherein the foaming composition further comprises a surfactant.

6. A foam according to claim 5 wherein the foaming composition further comprises a catalyst.

7. A foam according to claim 6 wherein the catalyst is an organic or inorganic acid.

8. A foam according to claim 1 wherein the resin is a phenol-formaldehyde resol resin and the foaming composition further comprises a nonionic surfactant.

9. A foam according to claim 8 wherein the foaming composition further comprises a catalyst containing xylene and toluene sulphonic acids.

10. A foam according to claim 8 wherein the blowing agent includes a fluorocarbon.

11. A foam according to claim 8 wherein the blowing agent includes a perflouroalkane.

12. A foam according to claim 8 wherein the foaming composition further comprises
   (iii) a nonionic surfactant and
   (iv) an acid catalyst.

* * * * *